(12) United States Patent
Fromherz et al.

(10) Patent No.: US 6,570,196 B1
(45) Date of Patent: May 27, 2003

(54) LIPID VESICLES OR LIPID BILAYERS ON CHIPS

(75) Inventors: Peter Fromherz, München (DE); Volker Kiessling, München (DE); Karsten Kottig, Planegg (DE); Günther Zeck, München (DE)

(73) Assignee: Max-Plank-Gesellschaft zur Forderung der Wissenschaften, Munich (DE)

( * ) Notice: Subject to any disclaimer, the term of this patent is extended or adjusted under 35 U.S.C. 154(b) by 0 days.

(21) Appl. No.: 09/532,872

(22) Filed: Mar. 22, 2000

(51) Int. Cl.⁷ ............... H01L 29/76; H01L 27/148; H01L 29/768
(52) U.S. Cl. ............... 257/213; 257/226; 257/227; 257/244
(58) Field of Search ............... 424/400, 450; 257/213, 226, 227, 244

(56) References Cited

U.S. PATENT DOCUMENTS

| 5,571,568 A | * 11/1996 | Ribi et al. |
| 5,783,566 A | * 7/1998 | Mislick ............... 514/44 |
| 5,830,430 A | * 11/1998 | Unger et al. |
| 6,331,289 B1 | * 12/2001 | Klaveness et al. ......... 424/9.52 |

* cited by examiner

Primary Examiner—Thurman K. Page
Assistant Examiner—Humera N. Sheikh
(74) Attorney, Agent, or Firm—Rothwell, Figg, Ernst & Manbeck

(57) ABSTRACT

The present invention relates to bioelectronic devices comprising lipid vesicles which are in contact with a chip, particularly with at least one gate of a field effect transistor. The vesicles/bilayers may comprise effector molecules in their membrane and thus are suitable as bioelectronic sensors. The chip may also have a capacitive stimulating spot, with which the electrical or functional state of the membrane or its incorporated molecules may be affected.

17 Claims, 6 Drawing Sheets

Fig.2a
Fig.2b
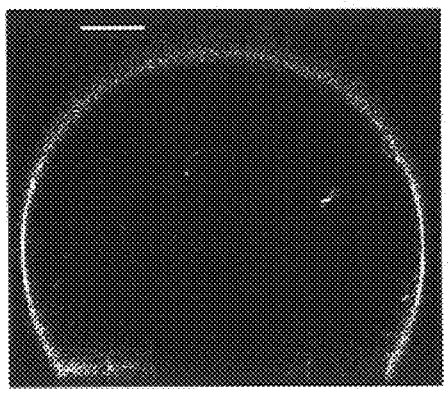
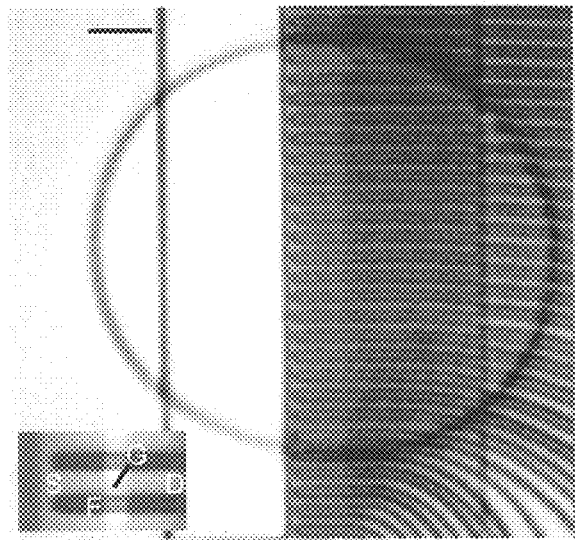

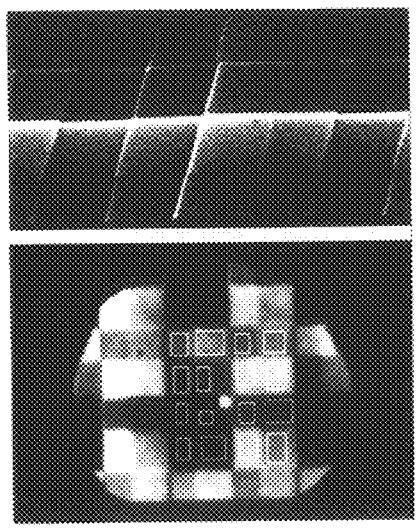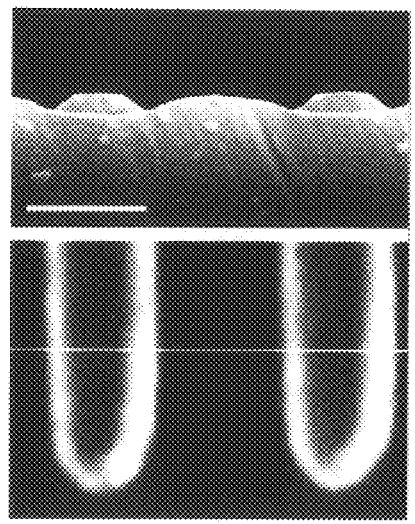
Fig.3a Fig.3b Fig.3d Fig.3e

LIPID VESICLES OR LIPID BILAYERS ON CHIPS

The present invention relates to bioelectronic devices comprising lipid vesicles which are in contact with a chip, particularly with at least one gate of a field effect transistor. The vesicles/bilayers may comprise effector molecules in their membrane and thus are suitable as bioelectronic sensors. The chip may also have a capacitive stimulating spot, with which the electrical or functional state of the membrane or its incorporated molecules may be affected.

So far, membrane-semiconductor contacts have been made by either (a) depositing monomolecular films or spreading lipid vesicles (Fromherz et al., Ber. Bunsenges. Phys. Chem. 84 (1980), 1045; Tamm et al., Biophys. J. 47 (1985), 105; Kalb et al., Biochim. Biophys. Acta 1103 (1992), 307; Sackmann, Science 271 (1996), 43; Gritsch et al., Langmuir 14 (1998), 3118) or (b) spanning a bilayer over a shallow groove (Fromherz and Klingler, Biochim. Biophys. Acta 1062 (1991), 103; Rentschler and Fromherz, Langmuir 14 (1998), 577). The first approach is prone to defect formation with a low resistance of the membrane; the second method implies a large distance between membrane and support with a low resistance of the cleft. In order to avoid these defects a pre-formed lipid vesicle was attached to a silicon chip with integrated transistors. As a result we obtained microscopic membrane-junctions with 100 GΩ resistances of membrane and cleft.

Thus a subject matter of the present invention is a bioelectronic device comprising (a) at least one lipid vesicle or a portion thereof (ruptured vesicle) comprising a membrane and (b) at least one electrode having at least one potential sensitive surface area or capacitive stimulating spot, wherein the membrane is in close contact with said area or stimulating spot.

BRIEF DESCRIPTION OF THE DRAWINGS

FIG. 2a represents a cross-section of a fluorescent vesicle on a chip.

FIG. 2b represents a micrograph of a vesicle on an array of transistors.

FIG. 3a represents a scanning electron micrograph of a silicon chip.

FIG. 3b represents a fluorescence micrograph of an attached membrane.

FIG. 3d represents a scanning electron micrograph of a section through a transistor.

FIG. 3e represents a fluorescence micrograph of a membrane on a chip.

Figure 1A:
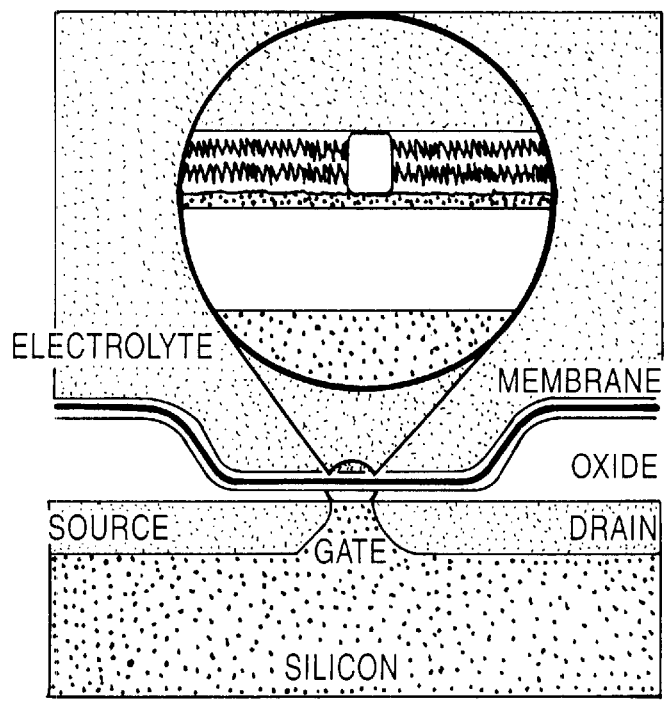
FIG. 1a depicts a lipid bilayer.
Figure 1B:
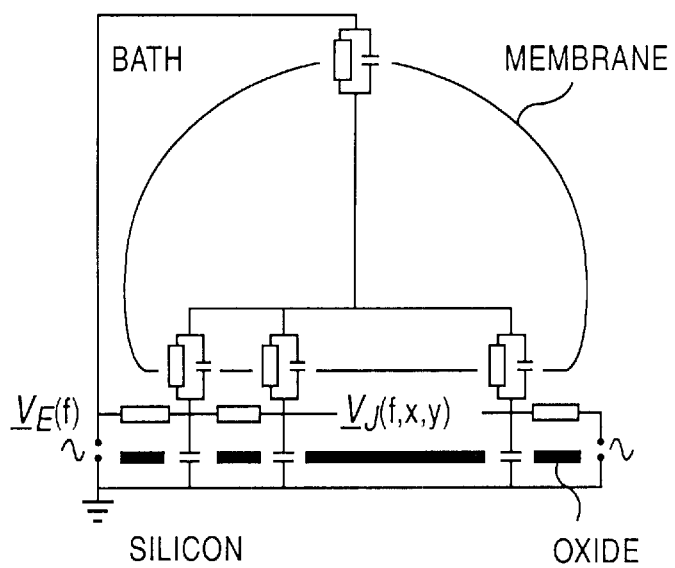
FIG. 1b depicts an AC circuit of planar core-coat conductor.
Figure 1C:
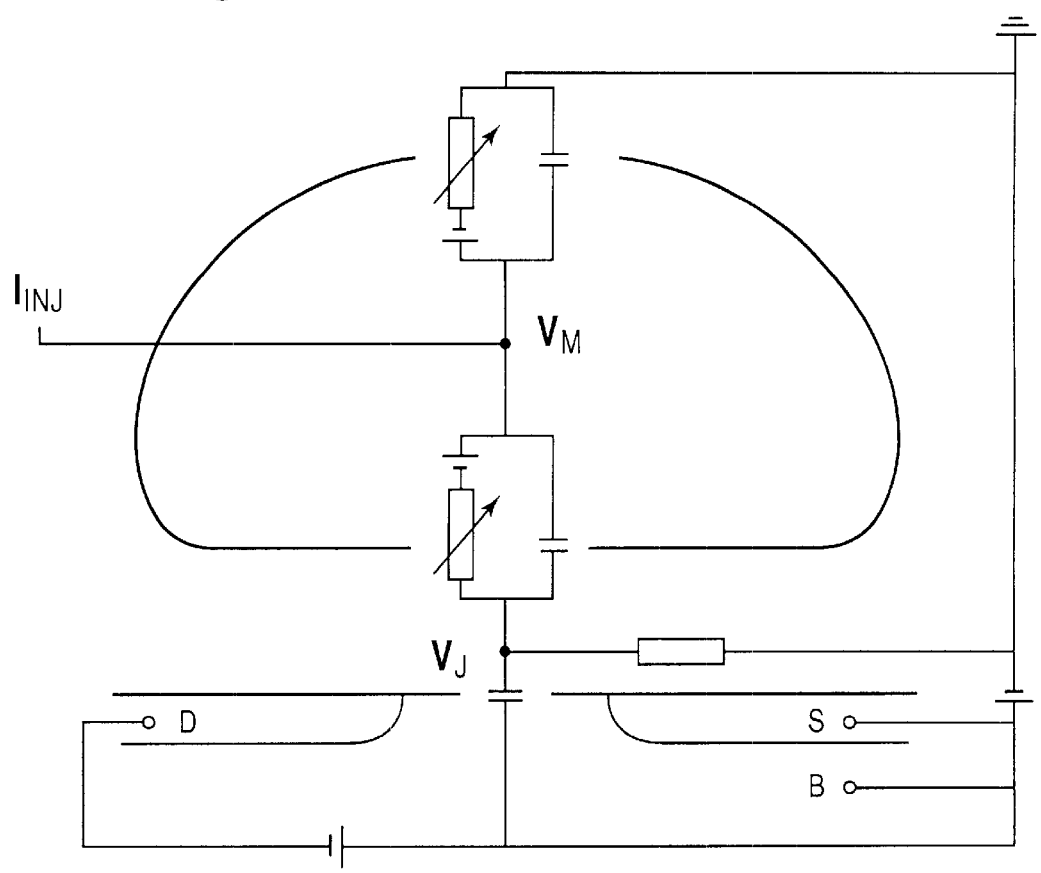
FIG. 1c depicts an equivalent circuit of the planar core-coat conductor in a point-contact model.

When a lipid vesicle or portion thereof is attached to the electrode surface, which may be oxidized silicon, other insulated semiconductors or metal, the cell membrane and the electrode surface are separated by a cleft which may be filled with an electrolyte as illustrated in FIG. 1. Preferably, the membrane of the vesicle or portion thereof is a lipid bilayer membrane. More preferably, the membrane comprises molecules having charged amphiphilic groups such as phospholipids. The vesicle size is preferably selected such that the vesicle extends beyond a potential sensitive area of the chip surface, e.g. in a range of from about 1 to about 1000 $\mu$m, preferably from 5 to 500 $\mu$m. Thus, a sandwich structure is formed of e.g. silicon, silicon dioxide, cleft, membrane and vesicle interior. This extended layered system is a planar electrical core-coat conductor: The conductive cleft is insulated by the thin films of silicon dioxide and membrane from the conductive phases of silicon and vesicle interior, respectively. The electrical resistance between membrane and cleft is preferably at least 1 MΩ, more preferably at least 1 GΩ, e.g. about 10 to 100 GΩ. This system may be described as an electrical circuit on the basis of which a fundamental coupling relation for bioelectronic sensors may be derived.

The electrode may be integrated on, e.g. embedded in a chip. The chip may comprise further devices such as stimulation spots, transistors etc. Preferably, the chip has at least one integrated field-effect transistor comprising at least one source and drain or an electrode as stimulation spot for applying voltages.

The equivalent circuit of the planar core-coat conductor in a vesicle-silicon junction is shown in FIGS. 1b+c. Capacitances are assigned to the membrane and to the oxide in the junction. One or several ion conductances in the attached membrane may be driven by Nernst potentials. The extended cleft is represented by an ohmic conductance. The free part of the vesicle is described by a capacitance and one or several ion conductances, too. The ionic and capacitive currents in the circuit determine the intracellular voltage $V_M$ and the extracellular voltage $V_J$ in the cleft. The voltage $V_J$ in the junction controls the transistor. It plays the same role as the gate-voltage on the metalized gate of a common MOS-FET.

We apply Kirchhoff's law to the node in the junction of FIG. 1b, and obtain Eq. 1 for the voltage $V_J$, with the membrane capacitance per unit area $c_M$, the ion conductance $g^1_{JM}$ per unit area of the membrane in the junction, the reversal voltage $V^1_0$ and a cleft conductance $g_J$ per unit area of the junction. The approximation of Eq. 1 is valid for weak coupling, i.e. for small values of $V_J$ and $dV_J/dt$ at a modest electrode capacitance $c_{OX}$.

$$g_J V_J = g^1_{JM}(V_M - V^1_0) + c_M \frac{dV_M}{dt} \quad (1)$$

The properties of the planar core-coat conductor are "squeezed" into the cleft conductance $g_J$ per unit area of the junction according to Eq. 2 with the distance $d_J$ of membrane and substrate, with the specific resistance $\rho_J$ of the electrolyte in the cleft and with the radius $a_J$ of a circular junction.

$$g_J = \frac{5\pi d_J}{\rho_J} \frac{1}{\pi a_J^2} \quad (2)$$

We may eliminate the capacitive current in Eq. 1 by taking into account Kirchhoff's law for the intracellular node of FIG. 2. The capacitive current through the total vesicle is balanced by the total ion current through the free and the attached areas of the membrane according to Eq. 3, with the specific conductances $g^1_{FM}$ and $g^1_{JM}$ in the two regions and with the ratio $\beta$ of the areas of attached and free membrane. Again the approximation of Eq. 3 is valid for weak coupling, i.e. for small values of $V_J$ and $dV_J/dt$.

$$(1+\beta)c_M \frac{dV_M}{dt} = -(g^1_{FM} + \beta g^1_{JM})(V_M - V^1_0) \quad (3)$$

Inserting Eq. 3 into Eq. 1, taking into account Eq. 2, we obtain the coupling relation for an ionoelectronic sensor according to Eq. 4.

$$V_J = \frac{\rho_J a_J^2}{5 d_J} \frac{g^1_{JM} - g^1_{FM}}{1+\beta}(V_M - V^1_0) \quad (4)$$

The relation shows that a large signal on the gate requires:
(i) a small distance $d_J$ of membrane and substrate,
(ii) a large radius $a_J$ of the contact,
(iii) an enhanced or depleted conductance of the receptor channels in the attached membrane with $g^1_{JM}-g^1_{FM} \neq 0$, and
(iv) an electrochemical driving force $V_M-V^1_0$.

In a preferred embodiment the lipid vesicle is attached to the electrode surface such that under operational conditions substantially no displacement of the vesicle takes place. The attachment may be effected by electrostatic interactions, entropic interactions, biospecific (e.g. protein-protein) interactions, van der Waals interactions, gravitation or any combination thereof. More particularly, a lipid vesicle having a membrane containing charges, e.g. negatively charged phospholipids, is attached to a surface which may be coated with an oppositely charged polyelectrolyte, e.g. a positively charged polyelectrolyte such as polylysine.

In a particularly preferred embodiment of the invention the lipid vesicle comprises a membrane having incorporated at least one functional molecule, i.e. a molecule which is capable of mediating electrically measurable effects due to environmental changes. These environmental changes may be changes in pH, temperature, concentrations of specific compounds in the medium and/or in the vesicle, temperature. Preferably, the functional molecule is a substance capable of integrating into lipid bilayer membranes, preferably a signalling substance which is capable of modulating its conformational or functional state in response to a change in the environment which may result from changes in environmental biological, chemical or physical parameters, e.g. the concentration of substances, changes in electrical states etc. The substance may be a biomolecule such as a protein, e.g. a transmembrane protein, particularly a channel-forming protein such as an ion channel and/or a ligand-specific receptor (e.g. Acetylcholin (ACh-receptor) which is a chemical gated ion channel conductive for $Na^+$, $K^+$ and $Ca^{2+}$ ions in the presence of ACh. The substance may also be a synthetic molecule, e.g. a low-molecular drug etc. The functional molecule may be a complex structure, e.g. a plurality of single molecules or molecule units, if a signal cascade is involved. This can be second messenger systems and signal pathways, containing G-proteins, e.g. the retinal light receptor rhodopsin. The molecular sensor, which is incorporated in the membrane may even be artificially designed for its specific function.

On the other hand, the conformational or functional state of a molecule, which is incorporated in the membrane, could be controlled by modulating the membrane potential via electrodes, which are integrated in a chip.

Thus, the bioelectronic device of the invention is suitable as a sensor which allows the determination of a change in an environmental parameter, e.g. a (pharmaceutical) substance in low concentrations, as a detectable signal on the electrode and it may be suitable as a scientific tool for studying the conformational and functional states of membrane proteins. When the functional molecule incorporated in the lipid membrane comprises an appropriate receptor optionally in combination with an ion channel, the bioelectronic device may be used in pharmaceutical testing procedures, which become cheaper and more efficient. Thus, the functional molecule can represent a highly sensitive sensoring system for mechanical, chemical, electrical or optical signals. The device of the present invention comprising a lipid membrane having incorporated thereto a functional molecule and a planar potential-sensitive electrode integrated in a proper substrate, e.g. an aqueous medium, combines the biological sensoring systems with the advantages of electronic signal processing.

By coupling the membrane to a semiconductor potential-sensitive electrode, changes in the characteristics of membrane-integrated functional molecules can be observed without electrochemical perturbations by probing the electrical state of the membrane and/or by directly probing the conformational changes of the integrated molecules.

For all applications as described above a sufficient electrical insulation between the coupling region between electrode surface and membrane and the surrounding medium, e.g. an electrolyte, is preferred.

Further, the invention shall be explained by the following figures and examples:

FIG. 1:
a) A lipid bilayer follows the surface profile of a metal-free field-effect transistor with thin gate oxide and thick field oxide. Membrane and oxide are separated by a cleft of electrolyte. The insert is scaled with a membrane thickness of about 4 nm. The white box symbolizes a functional molecule (e.g. membrane-protein).
b) AC circuit of planar core-coat conductor formed by the sandwich electrolyte-membrane-cleft-oxide-silicon in the attached region of a vesicle. It is probed by AC voltages $V_E(f)$ of frequency f applied to the bulk electrolyte. The voltage profile $V_J(x, y, f)$ in the junction is recorded with an array of transistors.
c) Equivalent circuit of the planar core-coat conductor in a cell/vesicle-transistor junction (point-contact model). The width of the cleft between membrane and chip is blown up. Source (S), drain (D) and bulk silicon (B) are kept at bias voltages with respect to the bath. The intracellular voltage $V_M$ and the extracellular voltage $V_J$ depend on the capacities of the attached and free membrane, on one or several ion conductances—driven by Nernst-type batteries—, on the stray capacitance of the chip and on the conductance of the cleft. A substance in the bath which opens ion channels affects conductances in the attached and free membrane. The resulting change of the voltage $V_J$ is detected by the transistor. An injection current $I_{INJ}$ can be applied by an impaled or fused micropipette.

FIG. 2:
Giant lipid vesicles on a silicon chip. Scale bars 10 $\mu$m.
a) Cross-section of a fluorescent vesicle on a chip with transistors obtained by laser scanning microscopy. The intensity of the attached membrane is inhomogeneous due to the variable thickness of silicon dioxide.
b) Micrograph of a vescicle on an array of transistors with a lattice constant 3.6 $\mu$m. The picture is aligned with a).

The insert shows the geometry of source (S), drain (D), local field oxide (F) and gate (G). The size of the gate is 2 μm×1.8 μm.

Distance measurement by fluorescence interference contrast (FLIC) microscopy.

FIG. 3:
a) Scanning electronmicrograph of a silicon chip with terraces of oxide (2.5 μm×2.5 μm) (16 heights from 30 nm to 320 nm).
b) Fluorescence micrograph of an attached membrane.
c) Intensity of selected areas in b) versus oxide thickness. The data are fitted with an optical theory. In the average of 30 measurements the distance between membrane and oxide was $d_{cleft}=(1.1\pm0.2)$ nm.
d) Scanning electronmicrograph of a section through a transistor after HF dip (scale bar 2 μm). The ripples in the silicon substrate are due to grinding. The two mounds are sections through the local field oxide.
e) Fluorescence micrograph of a membrane on the chip. The picture is aligned with d).
f) Profile of fluorescence along the line in e). Drawn: experiment. Dotted: optical theory with a distance $d_{cleft}=1.1$ nm between the membrane and oxide.

FIG. 4:
Fluidity measurement of fluorescence recovery after photobleaching (FRAP). A vesicle was attached to a silicon chip with a homogeneous 100 nm thick oxide.
a) Selected profiles of fluorescence at different delays (increment 0.96 s) after bleaching with a focused laser beam. Insert: micrograph just after bleaching (illumination time 320 ms). Scale bar 10 μm.
b) Variance of Gaussians fitted to the profiles versus time. The fit by linear regression leads to a diffusion coefficient of $D=3$ μm$^2$/s.

EXAMPLES

1. Materials and Methods

1.1. LiDid Vesicles

Negatively charged giant vesicles were prepared from the lipids palmitoyl-oleoyl-phosphatidyl-choline (POPC) and dioleoyl-phosphatidyl-methylester (DOPME) with the lipoid cyanine dye DilC$_{18}$ (molecular ratios 200:2:1) by the method of electroswelling. The vesicles contained 300 mM sucrose and were suspended in 300 mM glucose. The different densities of glucose and sucrose solutions promoted sedimentation. POPC (2 mM) (Avanti Polar Lipids, Alabaster), DOPME (20 μM) (Sigma, Heidelberg) and DilC$_{18}$ (10 μM) (Molecular Probes, Eugene) were dissolved in diethylether/methanol (volume ratio 9:1). 5 μl of the solution were applied to a pair of planar electrodes of indium tin oxide coated with 70 nm of silica. After drying, we added 1.25 ml of 300 mM sucrose and applied an AC voltage of 10 Hz, ramping the peak-to-peak amplitude from 100 mV to 6 V within 2 h. The attached vesicles were dissociated by applying an AC voltage of 4 Hz and 6 V amplitude for 20 min, with 1 Hz for 10 min and with 0.1 Hz for 10 min. We sucked 0.5 ml of the suspension into a wide pipette and added it to 2.5 ml of 300 mM glucose. 10 μl of that dispersion were applied to 2 ml of 300 mM glucose with 40 mM NaCl and 10 mM Tris/HCl buffer at pH 7.4 on a chip.

All the silicon chips had an all-oxide surface. They were cleaned by wiping with a 2% solution of an alkaline detergent (Tickopur RP100, Bandelin, Berlin) at 60° C., rinsed with milli-Q water and dried. Then they were coated with poly-L-lysine (MW 10.000, Sigma, Heidelberg) in milli-Q water (25 μg/ml) for 30 min at room temperature and rinsed 5 times with 40 mM NaCl, 300 mM glucose, 10 mM Tris/HCl at pH 7.4. The coating overcompensated the negative surface charge of silica. Then the vesicle suspension was applied. Individual sedimenting vesicles were adjusted before adhesion using a glass micropipette (opening 100 μm) in a stereomicroscope.

1.2 Fluorescence Interference Contrast Microscopy

We measured the distance between the membrane and silicon dioxide by fluorescence interference contrast (FLIC) microscopy. A vesicle was sedimented on a chip with microscopic terraces of oxide (2.5 μm×2.5 μm) (16 heights, 30 nm to 320 nm). Fluorescence micrographs were taken through a water immersion objective (100×, numerical aperture 1.0) (Zeiss Axioskop) by using a CCD camera with long time exposure (excitation 546 nm, detection 580–640 nm, time 320 ms). The fluorescence intensities were fitted with a multireflection, finite aperture theory for excitation and for emission. A change in the fluorescence lifetime due to radiative and nonradioative processes was taken into account using a quantum yield of fluorescence $\phi_F=0.34$. The distance $d_{cleft}$ of membrane and oxide was evaluated for a refractive index of $n_{cleft}=1.33$ in the cleft.

We used FLIC microscopy to check the distance of membrane and surface of transistors. Those chips had a distinct surface profile. We observed the pattern of fluorescence of attached vesicles across the profile and compared it with the computed intensity. The local thickness of the oxide and the local slope of the surface was obtained from scanning electromicrographs of cross sections. We used a simplified model of the FLIC theory: the transition moments of the dyes were oriented in parallel to the local inclination of the oxide, but the thickness of the local oxide was assumed to extend all over a planar silicon substrate. That approximation did not account precisely for effects of multireflection. The intensity profile obtained by local application of FLIC theory convoluted finally with the point transfer function of the microscope.

1.3 Fluorescence Recovery After Photobleaching

We measured the fluidity of the attached membrane by fluorescence recovery after photobleaching (FRAP). A vesicle was sedimented on a chip with a 100 nm thick homogeneous oxide. The dye of the bound membrane was bleached locally with a focused beam of an Argon laser at 514 nm for 5 s. Micrographs of the fluorescence were taken by a CCD camera with long time exposure (320 ms) under illumination with a Xe lamp. They were normalized by a micrograph taken before bleaching under identical conditions. We obtained averaged profiles of fluorescence by projecting the intensity of the bleached area onto a single radial coordinate. The profiles were fitted with Gaussians. The diffusion coefficient was obtained from the increase of the variance with time.

1.4 Transistor Recording

We attached giant vesicles onto chips with a linear array of 96 open transistors (lattice constant 3.6 μm). Bias voltages were applied to the bulk silicon, to the common source and between the drains and the source to define the working point of the transistors. The change of the source-drain current was calibrated for each transistor in terms of the voltage applied to the gate in electrolyte. We selected 36 transistors for measurements in the region of a giant vesicle. AC voltages $V_E(f)$ of frequency f (amplitude 20 mV) were applied to the bath with a Ag/AgCl electrode. The modulations of the source-drain current were transformed into voltages, amplified and fed into 36 custom-made two-phase lock-in amplifiers. The response was divided by the results of a reference measurement without vesicle. We obtained complex frequency-dependent profiles $V_J(x, f)$ of the AC voltage along the junction. The specific resistance $r_M$ of the membrane and the sheet resistance $r_J$ of the cleft were determined by comparing the normalized experimental profiles $V_J(x, f)/V_E(f)$ with theoretical profiles for a circular planar core-coat conductor.

2. Results

The negatively charged lipid vesicles were bound to oxidized silicon coated with poly-lysine in a shape of spherical caps with variable profile. Examples on a chip with a linear array of transistors are shown in FIG. 2 with an optical projection of an attached vesicle and with a section obtained by laser scanning microscopy. Appropriate cleaning and coating of the chip was crucial to avoid a burst of the vesicles upon attachment.

2.1 Distance of Membrane and Chip

Figure 3F:
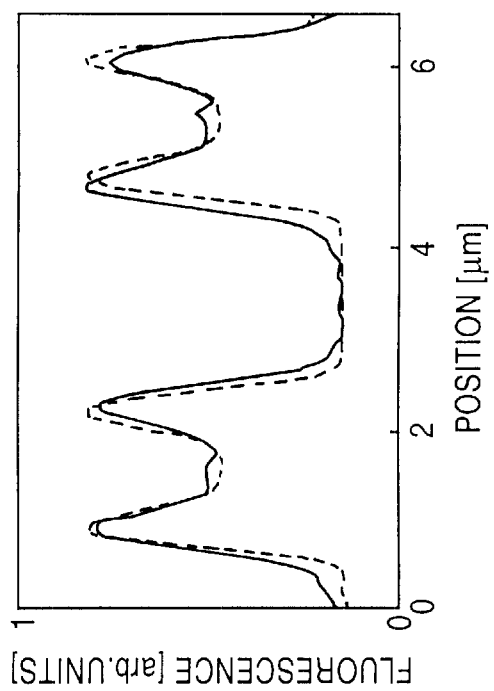
FIG. 3f represents a graph profile of fluorescence.
Figure 3C:
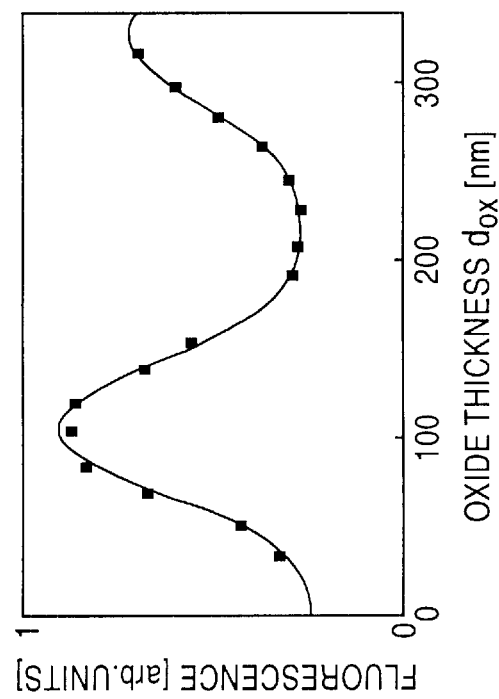
FIG. 3c represents the intensities of selected areas vs. oxide thickness.

The width of the cleft between membrane and silicon dioxide was determined by FLIC microscopy on silicon chips with microscopic terraces of oxide. An electronmicrograph of a chip is shown in FIG. 3a. The fluorescence of the attached membrane of a vesicle is shown in FIG. 3b. It was homogeneous on each terrace without fluctuations. We plotted the fluorescence intensity versus the thickness of the oxide as depicted in FIG. 3c and fitted the data by the FLIC theory. We obtained a distance $d_{cleft}$=1.1±0.2 nm (average of 30 measurements). Apparently, the attraction of membrane, poly-lysine and oxide was sufficient to overcome the repulsion by membrane undulations. On the other hand, the adhesion energy was not excessive such that it would induce a burst of the vesicles.

We studied the profile of the membrane on chips with transistors using FLIC microscopy. FIG. 3d shows the cross section of a chip with the regions of thick local oxide separating the gate areas with thin oxide. The fluorescence of an attached membrane was low on the gate oxide, higher on the field oxide, with a maximum on the slope as depicted in FIG. 3e. We computed the intensity profile with FLIC theory, assuming that the membrane followed the surface at a constant distance $d_{cleft}$=1.1 nm. We obtained two maxima of fluorescence on the slope between gate oxide (10 nm) and field oxide (400 nm), which fused to a single peak by convolution with the point transfer function of the microscope. The result was in good agreement with the experiment (FIG. 3f). It indicated that the membrane followed the surface without rupture and without spanning the grooves.

2.2 Membrane Fluidity

Figure 4A:
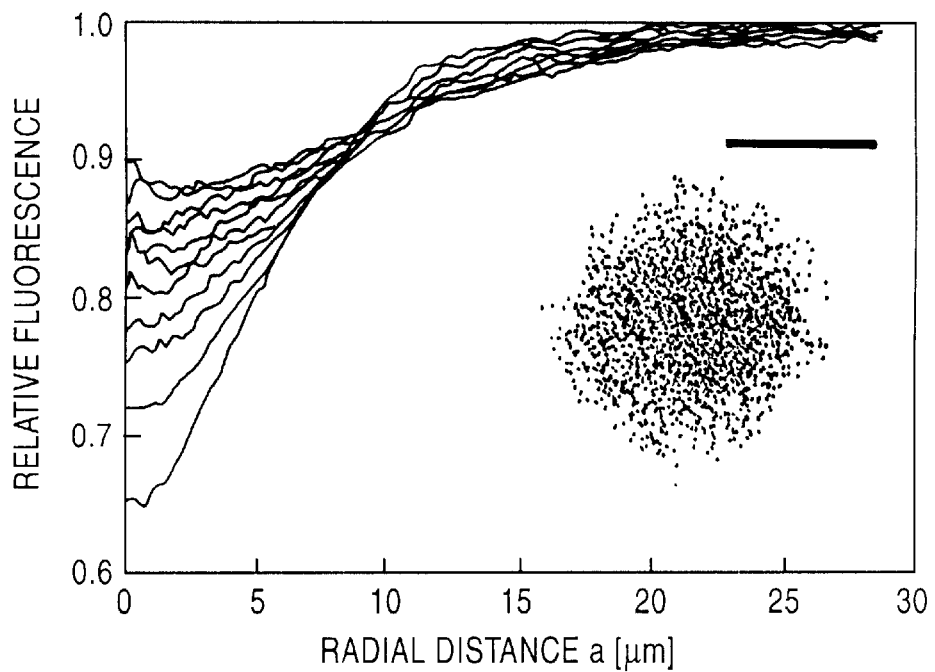
FIG. 4a depicts relative fluorescence vs. radial distance.
Figure 4B:
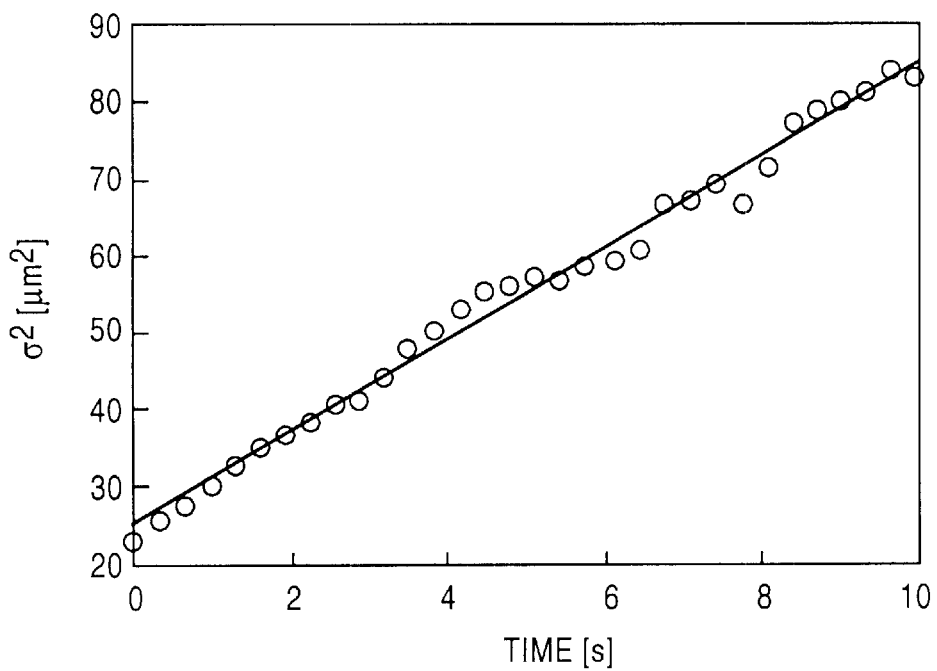
FIG. 4b depicts the variance of Gaussians fitted to the profiles vs. time.

We measured the fluidity of the attached membrane by fluorescence recovery after photobleaching on a chip with a 100 nm thick oxide. A set of radial profiles of fluorescence intensity is shown in FIG. 4a. The variance $\sigma^2$ of Gaussians fitted to the bleached spot increased with time t (FIG. 4b). We fitted the data by the linear relation $\sigma^2=\sigma^2_0+2$ Dt for normal diffusion. We obtained a diffusion coefficient D=3 $\mu m^2/s$. That value is typical for a fluid bilayer.

2.3 Resistances of Membrane and Cleft

We applied AC voltages $V_E(f)$ of frequency f to the bath and evaluated the voltage $V_J(x, f)$ along a row of transistors beneath an attached vesicle. At low frequency the whole junction followed the bath potential. There the coupling along the cleft dominated through ohmic conduction. The capacitive coupling through the membrane appeared in the center of the junction leading to a hammerlock-like voltage profile at a frequency as low as as 2 Hz. The transition was related with a dip of the phase.

We evaluated the specific resistance $r_M$ of the membrane and the sheet resistance $r_J$ of the cleft by comparing the experimental data with the theory of a circular planar core-coat conductor of radius $a_J$. The voltage along the radial distance a is given by Eq. 5 with the modified Bessel function $I_O$, the reciprocal length constant $\gamma$, the specific admittance $\gamma_M$ of the membrane, the specific capacitances $c_M$ and $c_{OX}$ of membrane and oxide and the ratio $\beta$ of the areas of attached and free membrane ($\omega=2\pi f$):

$$\frac{V_J(a, \omega)}{V_E(\omega)} = \frac{I_0(\gamma a)}{I_0(\gamma a_J)} + \frac{\gamma_M}{\gamma_M + i\omega c_{ox}}\left[1 - \frac{I_0(\gamma a)}{I_0(\gamma a_J)}\right], \quad (5)$$

$$\gamma^2 = r_J(\gamma_M + i\omega c_{ox}), \gamma_M = (r_M^{-1} + i\omega c_M)/(1 + \beta).$$

We used two sections of the data to fit the theory: the amplitude spectrum in the center of the junction at x=0 and the profile across the junction in the transition region at f=2 Hz. We assumed $a_J$=25 $\mu m$ as estimated from the observed width of the profiles, $\beta$=0.7 as estimated from the shape of the vesicles and $c_M$=0.6 $\mu F/cm^2$ of solvent free bilayers. From the fit we obtained $r_J$=130 G$\Omega$, $r_M$>1 M$\Omega cm^2$ and $c_{OX}$=0.35 $\mu F/cm^2$. It matches the data in all aspects. We studied twenty junctions and found reproducibly sheet resistances of $r_J$=50–130 G$\Omega$ and a membrane resistance of $r_M$>1 M$\Omega cm^2$.

Sometimes the vesicles burst after attachment and formed supported membrane fragments. Voltage profiles were measured also in these systems. They could be fitted with a membrane resistance $r_M$=10–100 k$\Omega cm^2$ at the sheet resistance of closed vesicles. Bursting weakened somewhat the compactness of the bilayer.

The addition of the channel-forming peptide gramicidin leads to drastic effects. When we added gramicidin C to the lipid mixture at a molar ratio 1:500, the junction followed the bath potential up to 10.000 Hz. There the junction switched from ohmic to capacitive coupling. The evaluation of the frequency dependent voltage profiles led to a membrane resistance of $r_M$=50 $\Omega cm^2$ at the sheet resistance given by the pure lipid membrane.

3. Discussion 3.1 Resistances

A sheet resistance $r_J$=100 G$\Omega$ at a thickness $d_{cleft}$=1.1 nm of the cleft corresponds to a specific resistance $\varrho_{cleft}$=11 k$\Omega cm$ using $r_J=\varrho_{cleft}/d_{cleft}$. For comparison, the specific resistance of the bulk electrolyte was 0.25 k$\Omega cm$. The density of mobile ions may be lowered by polyelectrolyte interaction of membrane, poly-lysine and oxide. Crucial is the dielectric effect of the two adjacent media with low dielectric constant—membrane and oxide—, considering that the width of the cleft is of the order of the Bjerrum length in water. Other measurements of the sheet resistance of supported bilayers on solids are not available.

A specific resistance $r_M$>1 M$\Omega cm^2$ is similar to that of a free-standing bilayer. The substrate does not induce electrical defects in the preformed bilayer despite the intimate attachment. Supported bilayers made by vesicle spreading or monolayer deposition on indium-tin oxide and gold are distinctly more leaky. Comparable data for bilayers on silicon are not available.

It might be noted (i) that the total membrane resistance of a junction with an area of 1.000 $\mu m^2$ (radius $a_J$=18 $\mu m$) is $R_{JM}=r_M/a^2_J\pi$>100 G$\Omega$ and (ii) that the seal resistance with respect to an ion channel (radius $a_{CH}$=1 nm) in the center is $R_J=(r_J/2\pi)$ ln $(a_J/a_{CH})$=160 G$\Omega$. Both values are similar to the resistance of a single ion channel in a membrane.

3.2 Feasibility of Molecular Interfacing

A bioelectronic device relies on local charge injection into the junction through the membrane by electroactive biomolecules or through the silicon dioxide by a capacitive effect (FIG. 1b). The resulting transient voltage $V_J$ in the junction forms the signal that mediates coupling. That signal fades away by charge spreading along the cleft and by charge relaxation across the membrane. The effect is described by Eq. 6 for a charge pulse $Q_0$ applied to the center of a circular contact when the contact is very large and when the upper membrane of the vesicle is negleced (t time).

$$V_J(a,t) = \frac{r_J Q_0}{4\pi t}\exp\left[-\frac{r_J(c_M+c_{ox})a^2}{4t}\right]\exp\left(-\frac{t}{r_M c_M}\right). \quad (6)$$

Charge relation through the membrane is slow. Its time constant is $r_M c_M \approx 1$ s for $r_M \approx 1$ M$\Omega$cm$^2$ and $C_M \approx 1$ $\mu$F/cm$^2$. On the other hand, the charge remains localized for only 1 ms within a radius of a=1 $\mu$m due to charge spread, even for $r_J \approx 100$ G$\Omega$ at $c_M + c_{OX} \approx 1$ $\mu$F/cm$^2$.

Consider an ion channel which opens for 100 $\mu$s at a conductance of 10 pS and a transmembrane voltage of 100 mV. It injects a charge of $10^{-16}$ As. Due to charge spread, the local voltage is around $V_J \approx 1$ mV after 1 ms. Such a local transient could be detected by a transistor with a gate size of 2 $\mu$m. A similar argument holds for the charge displacement created by a conformational change. However, to detect a charge displacement of about $10^{-19}$ As, an electronic device of smaller size and lower noise is required.

On the other hand, we may apply a voltage step of height $V_S$=3 V to a small stimulation spot with a radius of 100 nm and a specific capacitance $c_{OX}$=1 $\mu$F/cm$^2$. A charge of $10^{-15}$ As is injected into the junction. The voltage within 1 $\mu$m after 1 ms is around 10 mV, with a field-strength of 25.000 V/cm in the membrane. Such a local transient is able to affect molecular processes in the membrane.

When incorporating the channel-forming peptide gramicidin C into the vesicle membrane, the membrane properties were changed. Thus, a lower electrical resistance of the membrane could be detected with the field-effect transistor.

We conclude that a microscopic membrane-silicon junction with sufficient, e.g. 100 G$\Omega$ insulation—as achieved in the present study—provides a basis for the development of hybrid devices where biomolecules are addressed by microstructures and nanostructures in a semiconductor. If the close contact of membrane and substrate interferes with the function of a biomolecule—its lateral motion or its conformational change—, a local blister on the bilayer could be created by coating the chip locally with a protein that enhances the distance of membrane and chip.

What is claimed is:

1. A bioelectric device comprising
    a) at least one lipid vesicle or a portion thereof, comprising a membrane and
    b) at least one electrode having at least one potential sensitive surface area or capacitive stimulating spot,
    wherein the membrane is in close contact with said surface area or stimulating spot, and
    wherein the close contact between the membrane and the potential sensitive surface area of the chip comprises a cleft of from about 0.1 to about 200 nm in thickness.

2. The device of claim 1
    wherein the lipid vesicle or portion thereof comprises a membrane having incorporated at least one functional molecule.

3. The device of claim 2
    wherein said functional molecule is a protein.

4. The device of claim 2
    wherein said protein is selected from channels and receptors.

5. The device of claim 1
    wherein the lipid vesicle has a diameter of from about 5 to 500 $\mu$m.

6. The device of claim 1, wherein the electric resistance of the membrane and the cleft is at least about 1 M$\Omega$.

7. The device of claim 1, wherein the potential sensitive surface area of the electrode comprises oxidized silicon, an insulated semiconductor or metal.

8. The device of claim 1
    wherein the electrode is located on a chip.

9. The device of claim 8
    wherein the chip has at least one integrated field-effect transistor comprising at least one source and a drain or an electrode as stimulating spot for applying voltages.

10. The device of claim 9
    wherein the membrane is in close contact with at least one gate region between a source and a drain or stimulating spot.

11. The device of claim 1
    wherein the binding of lipid vesicle or portion thereof to the electrode surface comprises electrostatic interactions.

12. The device of claim 11
    wherein the electrode surface is coated with a polyelectrolyte.

13. The device of claim 12
    wherein the polyelectrolyte is polylysine.

14. A method for detecting a change in an environmental parameter comprising
    a) providing
        i) a bioelectric device of claim 1 comprising a membrane-integrated functional molecule capable of sensing the environmental parameter and mediating an electrically measurable effect from the environmental parameter, and
        ii) the environmental parameter,
    b) sensing the environmental parameter as an electronic signal on an electrode of the bioelectric device, and
    c) analyzing an electrical state of the membrane-integrated functional molecule through the electronic signal, wherein a change in the electrical state is a measure of the change in the environmental parameter.

15. The method of claim 14, wherein the environmental parameter is a biological, chemical or physical parameter.

16. The method of claim 15, wherein the environmental parameter is a pH, a temperature or a concentration for a compound.

17. The method of claim 14, wherein the functional molecule is a biomolecule, a synthetic molecule or a plurality of single molecules.

* * * * *